United States Patent [19]

Kunieda et al.

[11] Patent Number: 5,976,604
[45] Date of Patent: *Nov. 2, 1999

[54] OIL-IN-WATER EMULSION COMPOSITION HAVING HIGH OIL CONTENT AND METHOD FOR PRODUCING THE SAME

[75] Inventors: Hironobu Kunieda, Kanagawa; Kaoru Shioguchi, Tokyo, both of Japan

[73] Assignee: Mitsubishi Chemical Corporation, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/812,547

[22] Filed: Mar. 7, 1997

[30] Foreign Application Priority Data

Mar. 8, 1996 [JP] Japan .................................. 8-051597

[51] Int. Cl.$^6$ .................................. A23D 9/007
[52] U.S. Cl. .................. 426/602; 426/611; 252/302; 252/312; 424/438
[58] Field of Search .................. 426/611, 602; 252/302, 312; 424/438

[56] References Cited

U.S. PATENT DOCUMENTS

| | | | |
|---|---|---|---|
| 3,939,290 | 2/1976 | Terada | 426/602 |
| 4,940,601 | 7/1990 | Orphanos | 426/611 |
| 4,952,687 | 8/1990 | Bodor | 426/611 |
| 4,960,602 | 10/1990 | Talkington | 426/611 |
| 5,017,398 | 5/1991 | Jandacek | 426/611 |
| 5,366,753 | 11/1994 | Meyer | 426/611 |
| 5,431,949 | 7/1995 | Meyer | 426/611 |
| 5,472,728 | 12/1995 | Miller | 426/611 |
| 5,532,019 | 7/1996 | Miller | 426/611 |
| 5,837,300 | 11/1998 | Klemann | 426/611 |

FOREIGN PATENT DOCUMENTS

| | | | |
|---|---|---|---|
| 0291106 | 11/1988 | European Pat. Off. | 426/611 |
| 4234947 | 8/1992 | Japan . | |
| 678672 | 3/1994 | Japan . | |
| 787895 | 4/1995 | Japan . | |
| WO 91/15960 | 10/1991 | WIPO | 426/611 |

OTHER PUBLICATIONS

"The Structure of Gel–Emulsions in a Water/Nonionic Surfactant/Oil System", *Colloids and Surfaces,* 47 (1990) pp. 35–43.

"Effect of Types of Polyols on Surfactant Phase Emulsification", *Yukagaku,* 35 (1986), pp. 102–107.

English Abstract of JP 04234947 A.

English Abstract of JP 06078672 A.

English Abstract of JP 07087895 A.

"Effects and Properties of Ryoto Sugar Esters" *Ryoto Sugar Ester,* pp. 8–9, 20–21.

*Primary Examiner*—Carolyn Paden
*Attorney, Agent, or Firm*—Sughrue, Mion, Zinn, Macpeak & Seas, PLLC

[57] ABSTRACT

An oil-in-water emulsion composition having a high oil content, which comprises (a) a sucrose fatty acid ester, (b) water, and (c) an oily component, wherein (i) component (c) is present in an amount of 90% by weight or more based on the total weight of components (a), (b) and (c), (ii) at least 20% by weight of the fatty acid moiety constituting component (a) are derived from a saturated fatty acid having 8 to 16 carbon atoms, an unsaturated fatty acid having 16 to 22 carbon atoms, or a mixture thereof, and the proportion of a monoester in component (a) is 60% by weight or more; and a method for producing the oil-in-water emulsion composition having a high oil content, which comprises adding, to a mixture comprising the components (a), (b) and (c), a solid which is insoluble in the mixture in an amount of 0.01 to 10% by volume based on the total volume of the components (a), (b), and (c), followed by stirring and removal of the solid.

7 Claims, No Drawings

OIL-IN-WATER EMULSION COMPOSITION HAVING HIGH OIL CONTENT AND METHOD FOR PRODUCING THE SAME

FIELD OF THE INVENTION

The present invention relates to an oil-in-water (hereinafter, "oil-in-water" is sometimes abbreviated as "O/W") emulsion composition having a high oil content and a method for producing the same. More particularly, it relates to an oil-in-water emulsion composition having an oil content as high as 90% by weight or more and a method for producing the same. The composition of the present invention is used for medicines, cosmetics, foods, and the like.

BACKGROUND OF THE INVENTION

Oil-in-water emulsions having a high oil content are used as a cream preparation in the field of medicines and cosmetics or as a mayonnaise-like food in the field of foods. While those having a high oil content of 90% or more are generally difficult to prepare due to difficulty in emulsification and dispersion, it is known that polyoxyethylene surface active agents, which are regarded to have high emulsifying power amongst nonionic surface active agents, are capable of easily emulsifying and dispersing an oily component even in a proportion exceeding 90% (see H. Kunieda et al., *Colloids and Surfaces*, Vol. 47, p. 35 (1990) and Sagitani, et al., *Yukagaku*, Vol. 35, p. 102 (1986)).

However, polyoxyethylene surface active agents are known to have a high monomeric solubility in an oily component. Therefore, the surface active agent should be used in an amount of at least 20% by weight based on the total weight of the active agent and an aqueous component in order to obtain a stable oil-in-water emulsion having an oil content as high as 90% by weight or more. Further, since a polyoxyethylene emulsifier undergoes decomposition with the passage of time to produce formalin, this raises a safety problem, making it impossible to apply the resulting emulsion to foods, etc. In addition, when applied to creams or the like, there is another problem in that the emulsion is highly irritative to the skin.

SUMMARY OF THE INVENTION

An object of the present invention is to provide an oil-in-water emulsion composition having a high oil content, in which a large proportion of an oily component is stably emulsified with a small amount of a surface active agent and which has high safety, has no irritation to the skin, and is useful in the fields of medicines, cosmetics and foods.

The inventors of the present invention have carried out extensive studies for obtaining an emulsion which has excellent stability by using a small amount of a surface active agent even where the proportion of an oily component exceeds 80% by weight. As a result, they have found that an oil-in-water emulsion composition having a high oil content can be obtained by using a specific sucrose fatty acid ester as an emulsifier and thus completed the present invention.

The present invention relates to an oil-in-water emulsion composition having a high oil content, which comprises (a) a sucrose fatty acid ester, (b) water, and (c) an oily component, wherein (i) component (c) is present in an amount of 90% by weight or more based on the total weight of components (a), (b) and (c); (ii) at least 20% by weight of the fatty acid moiety constituting component (a) is derived from a saturated fatty acid having 8 to 16 carbon atoms, an unsaturated fatty acid having 16 to 22 carbon atoms, or a mixture thereof, and the proportion of a monoester in component (a) is 60% by weight or more. The present invention also relates to a method for producing the oil-in-water emulsion composition having a high oil content, which comprises adding, to a mixture comprising the components (a), (b) and (c), a solid which is insoluble in the mixture in an amount of 0.01 to 10% by volume based on the total volume of said components (a), (b), and (c), stirring the resulting mixture for emulsification, and removing the solid.

DETAILED DESCRIPTION OF THE INVENTION

The composition according to the present invention and a method for producing the same will hereinafter be described in detail.

1. Oil-in-water emulsion composition having a high oil content

Sucrose Fatty Acid Ester

Specific examples of the sucrose fatty acid ester comprising a saturated fatty acid having 8 to 16 carbon atoms, an unsaturated fatty acid having 16 to 22 carbon atoms, or a mixture thereof include sucrose caprylate, sucrose caprate, sucrose laurate, sucrose myristate, sucrose palmitate, sucrose palmitoleate, sucrose oleate, sucrose linoleate, sucrose linolenate, sucrose eicosatrienoate, sucrose arachidonate, sucrose erucate, sucrose docosahexaenoate, and mixtures of two or more thereof. Among these sucrose fatty acid esters, sucrose laurate and sucrose oleate are preferable. With respect to the sucrose fatty acid esters used in the present invention, at least 20% by weight, preferably 30% by weight, of the fatty acid moiety constituting the sucrose fatty acid ester are derived from a saturated fatty acid having 8 to 16 carbon atoms, an unsaturated fatty acid having 16 to 22 carbon atoms, or a mixture thereof. The other fatty acid moieties are not particularly limited and may be those derived from any fatty acids or a mixture thereof other than a saturated fatty acid having 8 to 16 carbon atoms and an unsaturated fatty acid having 16 to 22 carbon atoms. Examples of the sucrose fatty acid ester having such constituting fatty acids include sucrose stearate, sucrose arachate, and sucrose behenate. The proportion of the monoester in the sucrose fatty acid ester is not less than 60% by weight, preferably not less than 65% by weight, still preferably not less than 70% by weight.

As the weight proportion of monoesters in the sucrose fatty acid ester decreases, the sucrose fatty acid ester tends to form lamellar liquid crystals in an aqueous solution. In the practice of the present invention, it is considered that formation of lamellar liquid crystals makes it difficult to emulsify a large quantity of an oily component.

Since sucrose fatty acid esters have a highly lipophobic hydroxyl group in the hydrophilic moiety (i.e., sucrose moiety), they have lower monomeric solubility in an oily component than polyoxyethylene nonionic surface active agents. Even if a large quantity of an oily component is used as a disperse phase in an oil-in-water emulsion, a sucrose fatty acid ester is hardly dissolved in the oily component. That is, a sucrose fatty acid ester which is expected to act as a surface active agent on the oil/water interface suffers from no loss. Thus, the sucrose fatty acid ester, when used in a lesser amount as compared with the polyoxyethylene surface active agents, can provide a highly stable oil-in-water emulsion having a high oil content.

Water

Deionized water is preferred for use as a component (b) of the present invention.

Oily Component

The oily component for use in the present invention is not particularly limited. Useful oily components include hydrocarbons such as n-heptane, n-octane, n-decane, cyclohexane, hexadecane, squalene, squalane, and liquid paraffin; ethers such as diheptyl ether; diethers such as ethylene glycol dibutyl ether; long-chain amino-alcohols such as sphingosine; long-chain aldehydes; long-chain ketones; terpenoids; steroids; carotinoids; waxes; acyl glycerols; ether glycerides; ceramides; phospholipids; glycolipids; phosphoglycolipids; sulfolipids; and amino acid lipids. Mixtures of synthetic or natural fats and oils or mineral oils, such as vaseline, fish oil, olive oil, soybean oil, and glycerol tri(2-ethylhexanoate), are also useful.

In particular, the present invention provides a stable oil-in-water emulsion composition with oil components which are used in cosmetics or foods, such as hydrocarbons (e.g., n-octane, n-decane, hexadecane, squalene, squalane, and liquid paraffin) or fats and oils (e.g., glycerol tri(2-ethylhexanoate) and olive oil).

Composition

The proportion of component (c) of the oil-in-water emulsion composition according to the present invention is 90% by weight or more, preferably 93% by weight or more, still preferably 95% by weight or more, generally up to 99% by weight, based on the total weight of component (a) (i.e., sucrose fatty acid ester), component (b) (i.e., water), and component (c).

The sum of the components (a) and (b) is in a proportion of not more than 10% by weight, preferably not more than 7% by weight, more preferably from 1 to 5% by weight, based on the total weight of components (a), (b), and (c). The ratio of component (a) to component (b) can be chosen from a broad range. For example, component (a) can be used in an amount of 0.5 to 40% by weight based on the total weight of components (a) and (b). Even if the concentration of component (a) acting as a surface active agent is low, for example, as low as 0.5 to 10% by weight, a stable emulsion composition can be obtained.

According to the present invention, such a large quantity of the oily component can be included in a stably emulsified state by the use of a much lesser amount of a surface active agent than in conventional oil-in-water emulsions having a high oil content, and the emulsion compositions of the present invention have extremely high safety. In addition, since an aqueous phase forms a continuous phase, the emulsion composition, when applied to the skin, causes little discomfort such as stickiness of the oily component, giving a refreshing feeling.

Additive Component

In addition to the sucrose fatty acid ester, water, and the oily component, the oil-in-water emulsion composition having a high oil content according to the present invention may contain salts or amphiphilic substances, if desired. Further, if desired, the aqueous phase may contain monohydric alcohols having 1 to 3 carbon atoms; saccharides such as glucose and oligosaccharides; straight-chain polyols such as glycerol, sorbitol, and ethylene glycol; sugar alcohols such as maltitol and reducing oligosaccharides; proteins; peptides; amino acid; mucopolysaccharides such as chondroitin sulfate and hyaluronic acid; and glycosides such as saponin.

If desired, the products to which the oil-in-water emulsion composition having a high oil content of the present invention is applied can contain appropriate perfumes, coloring matter, antiseptics, drugs, thickeners, chelating agents, and the like. Illustrative examples of the protein include lactic casein, sodium caseinate, soybean protein, ovalbumin, serum albumin, lactic globulin, gelatin, collagen, glutelin, and the like. Illustrative examples of the coloring matter include β-carotene, annatto extract, turmeric oleoresin, paprika color, safrole yellow, riboflavin, lac color, curcumin, and chlorophyll. Illustrative examples of the perfume include cinnamon oil, pepper oil, mint oil, peppermint oil, lemon grass oil, spearmint oil, ginger oil, parsley oil, celery oil, and carrot oil. Illustrative examples of the antiseptic include dehydroacetic acid, benzoic acid, salicylic acid, thimerosal, benzalkonium chloride, phenylmercuric nitrate, and benzyl alcohol. Illustrative examples of the drug include indomethacin and adriamycin. Illustrative examples of the thickener include gum arabic, tragacanth gum, and xanthan gum. Illustrative examples of the chelating agent include ethylenediaminetetraacetic acid (EDTA), nitrilotriacetic acid (NTA), and ethyleneglycol bis(2-aminoethylether) tetraacetic acid (EGTA).

2. Method for Producing Composition

The emulsion composition of the present invention can be obtained by mixing the components (a), (b), and (c) in prescribed amounts and vigorously stirring the mixture. At this time, component (a) must be dissolved in the mixed system completely. Accordingly, if component (a) used is solid at room temperature, it is added after being melted by heating or as previously dissolved in component (b).

However, the emulsion is a so-called metastable composition, and success in production is often dependent on the method employed. The oil-in-water emulsion composition having a high oil content of the present invention can easily be obtained by adding, to a mixture of components (a), (b), and (c), a solid which is insoluble in the mixture (hereinafter, sometimes referred to as "insoluble solid") in a small amount, followed by stirring.

The insoluble solid used in the present invention includes solids that have a large surface area or a minute structure but do not have mutual chemical action with the mixed system of components (a), (b) and (c), e.g., aggregation of a spherical solid or fibrous solid made by glass or cotton. The size and shape of the insoluble solid are not particularly limited as long as the insoluble solid does not interfere with stirring and can be easily removed by filtration or the like. For example, in the case of an insoluble solid having a spherical shape, the solid having a diameter in the range of from 0.1 to 10 mm can easily be handled and is preferable. The amount of the insoluble solid to be added is decided arbitrarily and appropriately by a researcher within the above range, i.e., in an amount of from 0.01 to 10% by volume based on the total volume of the components (a), (b), and (c). After emulsification, the insoluble solid used can easily be taken out of the system by filtration or centrifugation.

By the above-mentioned method, a desired composition can be obtained more easily in production of a stable emulsion than by stirring the whole system at one time, uniformly, and intensively, for example, imposing a considerably strong mechanical shear force on the whole system.

The stirring can be carried out simply, for example, by manual shaking for laboratory scale production. Even for large scale production, any special emulsifying machine is not required and a simple stirring machine is sufficient for the production. Examples of the stirring machine include a motor-driven stirring machine having an axis with short rotating blades, magnetic stirrer, and the like.

For example, a stable emulsion composition of the present invention can be obtained in the presence of the insoluble solid by stirring with a magnetic stirrer generally at 1,000 to 2,000 r.p.m. and at room temperature. However, without the insoluble solid, a stable emulsion composition cannot be obtained under the same condition.

Instead of using the insoluble solid, the emulsion composition of the present invention can also be obtained by stirring with an agitating blade or in a mixing vessel having a minute structure and a large surface area. For example, an agitating blade having reticulate-like spaces, an agitating blade having a minute convex structure, a mixing vessel equipped with a baffle having reticulate-like spaces, a mixing vessel equipped with a large number of baffles, or a combination thereof may be employed.

Where a composition containing more than 90% by weight of an oily component is desired, the composition can be obtained more easily by a method in which emulsification is started in a system containing the oily component in a proportion of about 90% by weight based on the total amount of the emulsion composition as a precursor, followed by gradual addition of the rest of the oily component, rather than by a method in which the whole oily component is emulsified at one time.

Thus, by the method according to the present invention, a stable system can be obtained with ease without relying on mechanical shear force and the labor in production can be reduced.

The oil-in-water emulsion composition having a high oil content obtained by the foregoing procedure may be used in foods, cosmetics, medicaments, and the like. In particular, it can be used in foods such as dressing, coffee whitener, mayonnaise, and margarine, cosmetics such as emollient cream, massage cream, cleansing cream, makeup cream, base cream, and pre-makeup cream, and medicaments such as a cream preparation in which an oil-soluble drug has been dissolved.

The present invention will now be illustrated in greater detail with reference to Examples, but it should be understood that the present invention is not to be construed as being limited thereto as far as it is within the scope of the present invention.

The fact that the emulsion prepared was O/W type was confirmed through observation under a microscope (the oil phase to aqueous phase volume ratio and a Becke line effect (see H. Kunieda et al., *Colloids and Surfaces*, Vol. 24, p. 225 (1987))) and through a diffusion test of the emulsion in water.

The formulation of the components and the oil to water ratio of the composition are shown in Table 1 below, and the composition of the fatty acids and the proportion of monoesters constituting the surface active agents used in Examples and Comparative Examples are shown in Table 2 below.

EXAMPLE 1

Sucrose monolaurate (SM-1200, produced by Mitsubishi Chemical Foods K.K.) dissolved in distilled water uniformly, and n-decane (guaranteed reagent, produced by Tokyo Kasei Kogyo K.K.) were put in a test tube with a screw closure, and 0.5% by volume of adsorbent cotton (adsorbent cotton according to *Japanese Pharmacopeia*, produced by Toei K.K.) was added thereto. The system was emulsified by shaking by hand at 25° C. to prepare an oil-in-water emulsion composition, then the cotton was taken out.

The resulting oil-in-water emulsion composition which was prepared of the method of the present invention was stable and shows no phase separation for 6 months at 25° C. and for 4 weeks at 40° C.

EXAMPLE 2

Sucrose monolaurate (SM-1200, produced by Mitsubishi Chemical Foods K.K.) dissolved in distilled water uniformly, and n-decane (guaranteed reagent, produced by Tokyo Kasei Kogyo K.K.) were put in a test tube with a screw closure, and 0.03% by volume of glass wool (Quartz Glass Wools Grade A, produced by Toshiba Ceramics Co., Ltd.) was added thereto. The system was emulsified by stirring with a magnetic stirrer at 1,500 rpm and at 25° C. to prepare an oil-in-water emulsion composition, then the glass wool was taken out.

The resulting oil-in-water emulsion composition which was prepared of the method of the present invention was stable and showed no phase separation for 6 months at 25° C.

EXAMPLE 3

Sucrose monolaurate (SM-1200, produced by Mitsubishi Chemical Foods K.K.) dissolved in distilled water uniformly, and n-hexadecane (guaranteed reagent, produced by Tokyo Kasei Kogyo K.K.) were put in a test tube with a screw closure, and the system was emulsified by the same method as in Example 1.

The resulting oil-in-water emulsion composition was stable and showed no phase separation for 6 months at 25° C.

EXAMPLES 4 AND 5

Sucrose monolaurate (SM-1200, produced by Mitsubishi Chemical Foods K.K.) dissolved in distilled water uniformly, and squalane (guaranteed reagent, produced by Tokyo Kasei Kogyo K.K.) were put in a test tube with a screw closure, and the system was emulsified by the same method as in Example 2.

The resulting oil-in-water emulsion compositions were stable and showed no phase separation for 1 month at 25° C. The composition of Example 5 showed no phase separation for 4 weeks at 40° C.

EXAMPLE 6

Sucrose monopalmitate dissolved in distilled water uniformly, and n-decane (guaranteed reagent, produced by Tokyo Kasei Kogyo K.K.) were put in a test tube with a screw closure, and the system was emulsified by the same method as in Example 1.

The resulting oil-in-water emulsion composition was stable and showed no phase separation for 1 month at 25° C.

EXAMPLE 7

Sucrose monooleate dissolved in distilled water uniformly, and n-decane (guaranteed reagent, produced by Tokyo Kasei Kogyo K.K.) were put in a test tube with a screw closure, and the system was emulsified by the same method as in Example 1.

The resulting oil-in-water emulsion composition was stable and showed no phase separation for 1 month at 25° C.

EXAMPLE 8

Sucrose laurate (L-1695, Mitsubishi Chemical Foods K.K.) dissolved in distilled water uniformly, and glycerol tri(2-ethylhexanoate) (TEH, produced by The Nisshin Oil Mills, Ltd.) were put in a test tube with a screw closure, and the system was emulsified by the same method as in Example 1.

The resulting oil-in-water emulsion composition was stable and showed no phase separation for 1 month at 25° C.

EXAMPLE 9

Sucrose stearate (S-1670, produced by Mitsubishi Chemical Foods K.K.) dissolved in distilled water uniformly, and n-decane (guaranteed reagent, produced by Tokyo Kasei Kogyo K.K.) were put in a test tube with a screw closure, and the system was emulsified by the same method as in Example 1.

The resulting oil-in-water emulsion composition was stable and showed no phase separation for 1 month at 25° C.

COMPARATIVE EXAMPLE 1

Sucrose monostearate dissolved in distilled water uniformly, and n-decane (guaranteed reagent, produced by Tokyo Kasei Kogyo K.K.) were put in a test tube with a screw closure, and 0.5% by volume of adsorbent cotton (adsorbent cotton according to *Japanese Pharmacopeia*, produced by Toei K.K.) was added thereto. The system was shaken by hand at 25° C.

The resulting composition showed phase separation immediately after preparation, failing to provide a stable oil-in-water emulsion composition.

COMPARATIVE EXAMPLE 2

Sucrose stearate (S-1170A, produced by Mitsubishi Chemical Foods K.K.; monoester: about 55 wt %) dissolved in distilled water uniformly, and n-decane (guaranteed reagent, produced by Tokyo Kasei Kogyo K.K.) were put in a test tube with a screw closure, and 0.5% by volume of adsorbent cotton (adsorbent cotton according to *Japanese Pharmacopeia*, produced by Toei K.K.) was added thereto. The system was shaken by hand at 25° C.

The resulting composition showed phase separation immediately after preparation.

In Table 1, the symbols have the following respective meanings.

⊚: No phase separation

○: Less than 5% phase separation, oil-in-water type x: Phase separation

-: No data

TABLE 1

| | Example 1 | Example 2 | Example 3 | Example 4 | Example 5 | Example 6 | Example 7 | Example 8 | Example 9 | Comparative Example 1 | Comparative Example 2 | Comparative Example 3 |
|---|---|---|---|---|---|---|---|---|---|---|---|---|
| Formulation: | | | | | | | | | | | | |
| Sucrose Fatty Acid Ester: | | | | | | | | | | | | |
| Monolaurate (SM-1200) | 0.3 | 0.2 | 0.1 | 0.2 | 0.4 | | | | | | | |
| Monopalmitate | | | | | | 0.06 | | | | | | |
| Monostearate | | | | | | | | | | 0.4 | | |
| Monooleate | | | | | | | 0.2 | | | | | |
| Laurate (L-1695) | | | | | | | | 0.05 | | | | |
| Stearate (S-1670) | | | | | | | | | 0.35 | | | |
| Stearate (S-1170) | | | | | | | | | | | 0.025 | |
| Stearate (S-770) | | | | | | | | | | | | 0.008 |
| Distilled Water | 2.7 | 3.8 | 2.9 | 2.8 | 7.6 | 5.94 | 3.8 | 3.75 | 6.65 | 7.6 | 4.975 | 7.992 |
| Oily Component: | | | | | | | | | | | | |
| Decane | 97.0 | 96.0 | | | | 94.0 | 96.0 | | 93.0 | 92.0 | 95.0 | 92.0 |
| Hexadecane | | | 97.0 | | | | | | | | | |
| Squalane | | | | 97.0 | 92.0 | | | | | | | |
| Glycerol tri(2-ethylhexanoate) | | | | | | | | 97.0 | | | | |
| Concentration of Sucrose Ester in Water (wt %) | 10.0 | 5.0 | 3.3 | 6.7 | 5.0 | 1.0 | 5.0 | 1.7 | 5.0 | 5.0 | 0.5 | 0.1 |
| Oil/Water Ratio | 97/3 | 96/4 | 97/3 | 97/3 | 92/8 | 94/6 | 96/4 | 97/3 | 93/7 | 92/8 | 95/5 | 92/8 |
| Emulsion Stability: | | | | | | | | | | | | |
| Immediately After Preparation | ⊚ | ⊚ | ⊚ | ⊚ | ⊚ | ⊚ | ⊚ | ⊚ | ⊚ | X | X | X |
| 25° C. x1 Month | ⊚ | ⊚ | ⊚ | ⊚ | ⊚ | ○ | ⊚ | ⊚ | ⊚ | — | — | — |
| 25° C. x6 Months | ⊚ | ⊚ | ⊚ | — | — | — | — | — | — | — | — | — |
| 40° C. x1 Week | ⊚ | — | — | — | ⊚ | — | — | — | — | — | — | — |

COMPARATIVE EXAMPLE 3

Sucrose stearate (S-770, produced by Mitsubishi Chemical Foods K.K.; monoester: about 40 wt %) dissolved in

TABLE 2

| Sucrose Fatty Acid Ester | Monoester Content (wt %) | Fatty Acid Composition (wt %) |
|---|---|---|
| Monolaurate (SM-1200) | ≧99 | Lauric acid: ≧95 |
| Monopalmitate | ≧99 | Palmitic acid: ≧95 |
| Monostearate | ≧99 | Stearic acid: ≧95 |
| Monooleate | ≧99 | Oleic acid: ≧95 |
| Laurate (L-1695) | 80 | Lauric acid: ≧95 |

TABLE 2-continued

| Sucrose Fatty Acid Ester | Monoester Content (wt %) | Fatty Acid Composition (wt %) |
|---|---|---|
| Stearate (S—1670) | 75 | Stearic acid: ca. 70<br>Palmitic acid: ca. 30 |
| Stearate (S—1170) | 55 | Stearic acid: ca. 70<br>Palinitic acid: ca. 30 |
| Stearate (S—770) | 40 | Stearic acid: ca. 70<br>Palmitic acid: ca. 30 |

The emulsion composition of the present invention exhibits emulsion stability even with such a high oil content as 90% by weight or more, which has been conventionally considered as being difficult to achieve. In the present invention, the surface active agents which are widely employed as food additives are used and stable emulsification of the oily component can be achieved at a small amount of the surface active agent, i.e., in a range of from 0.5 to 40% by weight based on the aqueous phase. Therefore, the emulsion composition of the present invention is of high practical use from the viewpoint of safety.

The emulsion composition of the present invention is also extremely valuable in industrial use. The present invention is applicable to creams emulsions such as cleansing cream, massage cream, emollient cream, and hair cream, and to foods, medicines, and the like. The continuous phase of the emulsion composition of the present invention is the aqueous phase. Accordingly, when the composition of the present invention in the form of a cream emulsion, etc., is applied to the skin, it gives a moistening and refreshing feeling to the skin without feeling sticky.

While the invention has been described in detail and with reference to specific embodiments thereof, it will be apparent to one skilled in the art that various changes and modifications can be made therein without departing from the spirit and scope thereof.

This application is based on Japanese patent application Hei-8-51597, filed on Mar. 8, 1996, incorporated herein by reference.

What is claimed is:

1. An oil-in-water emulsion composition having a high oil content, which comprises (a) a sucrose fatty acid ester, (b) water, and (c) an oily component, wherein
   (i) component (c) is present in an amount of 90% by weight or more based on the total weight of components (a), (b) and (c);
   (ii) at least 20% by weight of the fatty acid moiety constituting component (a) is derived from a saturated fatty acid having 8 to 16 carbon atoms, an unsaturated fatty acid having 16 to 22 carbon atoms, or a mixture thereof, and the proportion of a monoester in component (a) is 60% by weight or more.

2. The oil-in-water emulsion composition having a high oil content as claimed in claim 1, wherein at least 20% by weight of the fatty acid moiety constituting component (a) is derived from lauric acid, oleic acid, or a mixture thereof.

3. The oil-in-water emulsion composition having a high oil content as claimed in claim 1 or 2, wherein component (a) is present in an amount of 0.5 to 40% by weight based on the total weight of components (a) and (b).

4. A method for producing an oil-in-water emulsion composition having a high oil content;
   which oil-in-water emulsion composition comprises (a) a sucrose fatty acid ester which functions as an emulsifier, (b) water, and (c) an oily component, wherein:
   (i) component (c) is present in an amount of 90% by weight or more based on the total weight of components (a), (b) and (c);
   (ii) at least 20% by weight of the fatty acid moiety constituting component (a) is derived from a saturated fatty acid having 8 to 16 carbon atoms, an unsaturated fatty acid having 16 to 22 carbon atoms, or a mixture thereof, the proportion of a monoester in component (a) is 60% by weight or more, and the sum of components (a) and (b) is in a proportion of not more than 10% by weight, based on the total weight of components (a), (b) and (c);
   which method comprises adding, to a mixture comprising said components (a), (b) and (c), a solid which is insoluble in said mixture in an amount of 0.01 to 10% by volume based on the total volume of said components (a), (b), and (c),
   stirring the resulting mixture, and
   removing said solid.

5. The method of claim 4, wherein at least 20% by weight of the fatty acid moiety constituting component (a) is derived from lauric acid, oleic acid, or a mixture thereof.

6. The method of claim 5, wherein component (a) is present in an amount of 0.5 to 40% by weight based on the total weight of components (a) and (b).

7. The method of claim 4, wherein component (a) is present in an amount of 0.5 to 40% by weight based on the total weight of components (a) and (b).

* * * * *